United States Patent
Van Driel

[11] Patent Number: 5,908,048
[45] Date of Patent: Jun. 1, 1999

[54] DUST CAP FOR BARBED CONNECTORS

[75] Inventor: Michael R. Van Driel, Fountain Valley, Calif.

[73] Assignee: Medtronic, Inc., Minneapolis, Minn.

[21] Appl. No.: 08/940,070

[22] Filed: Sep. 29, 1997

[51] Int. Cl.[6] .............................. F16L 55/10; A61M 1/00
[52] U.S. Cl. ...................... 138/89; 138/96 R; 215/305; 215/317; 220/796; 220/DIG. 19
[58] Field of Search ................. 138/89.1–89.4, 138/89, 96 R, 96 T; 215/295, 305, 316, 317, 319; 220/796, 805, 287, DIG. 19

[56] References Cited

U.S. PATENT DOCUMENTS

| | | | |
|---|---|---|---|
| 2,161,097 | 6/1939 | Schroder-Nielsen | 215/317 X |
| 2,379,529 | 7/1945 | Kennedy | 138/96 R X |
| 2,461,620 | 2/1949 | Wright | 215/317 X |
| 2,573,552 | 10/1951 | Detzel | 138/96 R |
| 2,672,160 | 3/1954 | Wrabel | 138/89.2 |
| 2,873,765 | 2/1959 | Gregory | 138/96 R |
| 2,878,905 | 3/1959 | Langermeier | 138/89.3 X |
| 2,899,483 | 8/1959 | Robertson et al. | 138/96 R |
| 3,227,303 | 1/1966 | Krakowsky | 215/295 X |
| 3,305,120 | 2/1967 | Owen | 138/96 R X |
| 3,430,798 | 3/1969 | Goyet et al. | 215/295 |
| 4,095,810 | 6/1978 | Kulle | 138/96 R |
| 4,335,756 | 6/1982 | Sharp et al. | 138/96 R X |
| 4,483,371 | 11/1984 | Susin | 138/89.2 X |
| 4,779,997 | 10/1988 | Schmidt | 215/317 X |
| 4,991,629 | 2/1991 | Ernesto et al. | 138/96 R X |
| 5,280,809 | 1/1994 | Tive | 138/89.2 X |

FOREIGN PATENT DOCUMENTS 1300393   7/1969   Germany  ................. 138/89.3

*Primary Examiner*—Patrick Brinson
*Attorney, Agent, or Firm*—Harry G. Weissenberger

[57] ABSTRACT

A reusable dust cap for tubing connectors on medical devices has an internal shoulder or ridge which engages a barb or groove on the connector to hold the cap during shipment. A grasping nub is provided on the cap to allow the cap to be forcibly disengaged from the barb or groove by the end user.

2 Claims, 1 Drawing Sheet

DUST CAP FOR BARBED CONNECTORS

FIELD OF THE INVENTION

This invention relates to connector caps used on medical equipment or the like, and more particularly to a cap which positively and repeatedly snaps onto the connector yet is easily removable therefrom.

BACKGROUND OF THE INVENTION

Many kinds of medical devices made of rigid plastic such as, e.g. oxygenators and hard-shell venous reservoirs, use connectors molded into the body of the device to allow plastic tubing to be connected thereto. In oxygenator heat exchangers, for example, water connectors have an annular groove near their end, while oxygen connectors have annular barbs for holding tubing on the connector.

When such devices are packaged for shipment and sterilized, the connectors are closed off by sliding dust caps onto them. Conventionally, these are cylindrical devices, closed at one end, made of a soft, pliable plastic material such as plastisol (i.e. polyvinyl chloride with plasticizer) or, more expensively, polyolefin.

A significant problem with the prior art caps arises out of the fact that they rely on the elasticity of the cap material to hold them on the connector. The tolerances of the plastisol material (+1.5 to 0.8 mm) make it difficult to design an adequate and consistent tight fit of the cap onto the port, causing caps to sometimes fall off in shipment. Conversely, the plasticizer in the plastisol migrates out of the cap onto the connector with time and, with a tight fit, can eventually form a bond that makes the cap difficult to remove. Finally, from a manufacturing point of view, conventional caps are undesirable because an installer cannot readily tell if a cap has been pushed far enough onto a connector.

SUMMARY OF THE INVENTION

The invention solves the above-described problems of the prior art by providing a dust cap with an internal ridge or shoulder that snaps over a barb or into a groove of the connector for positive engagement. Because the user would find it difficult to disengage the cap from the connector merely by grasping its smooth, flat conventional gripping surface (which is particularly slippery when the cap has been rinsed with alcohol), the gripping surface of the cap of this invention is provided with a thickened nub which allows the user to get a good grip on the cap. Furthermore, unlike conventional caps, the inventive caps are reusable if it is desired to cap off a connector after use, or if a connector has been uncapped in error.

DESCRIPTION OF THE PREFERRED EMBODIMENT

Figure 1:
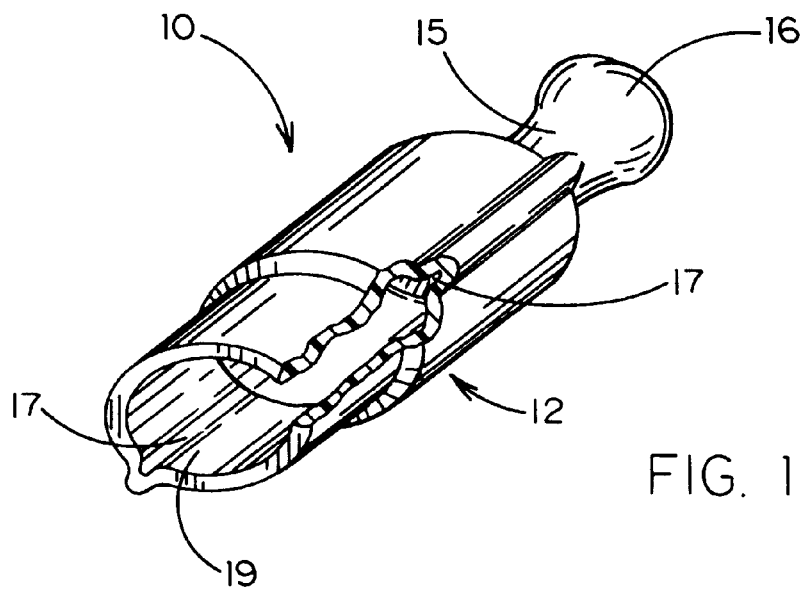
FIG. 1 is a partially cut-away perspective view of a first embodiment of the invention.
Figure 2:
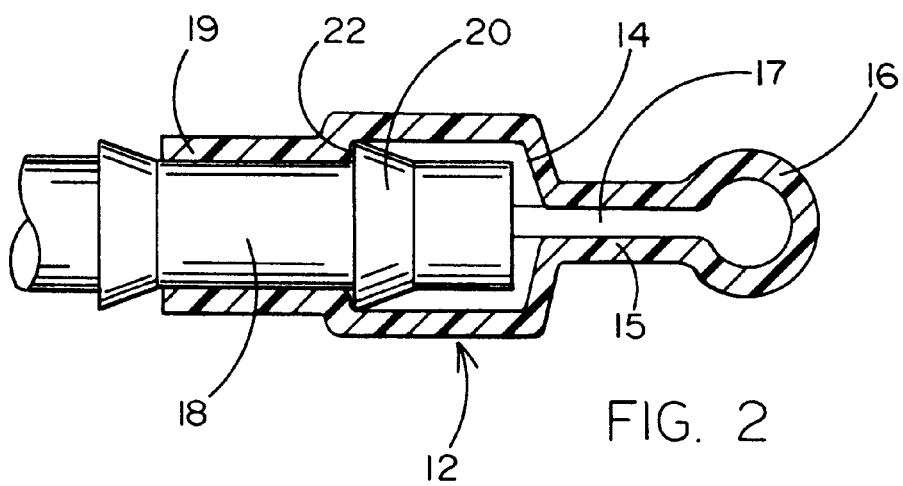
FIG. 2 is an axial section of the dust cap of FIG. 1 installed on a barbed connector.
Figure 3:
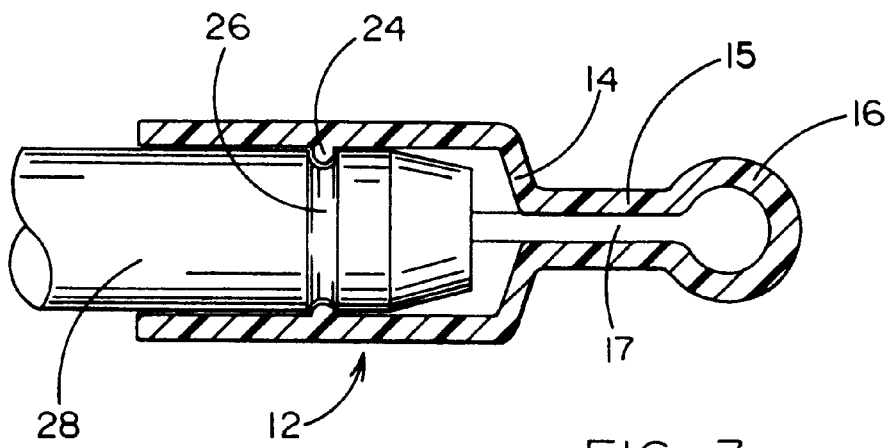
FIG. 3 is an axial section of an alternative embodiment of the invention installed on a grooved connector.

FIG. 1 shows the dust cap 10 of this invention. The dust cap 10 has a hollow cylindrical body 12 closed off at one end by a capping surface 14. A gripping surface 15 extends axially outwardly from the surface 14 and terminates in a thickened nub 16. The nub 16 is so shaped as to provide to the user a positive grip which allows the user to exert a substantial force on the body 12 when withdrawing the dust cap 10 from a connector 18 (FIGS. 2 and 3). The cap 10 is conventionally provided with grooves 17 to allow sterilization gases to penetrate into the interior of cap 10.

In one preferred embodiment of the invention, the open end 19 of the body 12 has a smaller inside diameter (ID) than the rest of the body 12. FIG. 2 illustrates how this smaller ID cooperates with a barb 20 on the connector 18 when installed thereon.

The material of the dust cap 10, which may be plastisol or any other conventional cap material, is sufficiently elastic to expand the cap 10, when slipped onto the connector 18, to the point where the smaller diameter portion 19 of the dust cap 10 rides over the barb 20. Once the portion 19 passes the barb 20, however, its elasticity causes it to contract so that the shoulder 22 engages the barb 20 and thus secures the cap 10 against unintentional removal from the connector 12. Accidental disengagement of the cap 10 from the barb 18 during shipment is thus prevented, and the elastic inward snapping of the portion 19 when it has cleared the barb 18 unequivocally signals the assembler that the cap 10 has been correctly positioned.

When the end user wishes to remove the cap 10, he grasps it by the nub 16 and pulls it sufficiently hard to cause the shoulder 22 and portion 19 to expand and ride over the barb 20. Because of the elasticity of the cap 10, this does not damage the cap 10, and it can be reused if necessary.

The positive engagement of the shoulder 22 with the barb 20 dispenses with the need for a tight fit between the cap 10 and the connector 18. Consequently, the cap 10 can be made loose enough to minimize plasticizer migration and the consequent sticking after lengthy storage.

FIG. 3 illustrates a second embodiment of the cap 10 in which the smaller ID portion 19 is replaced by an annular ridge 24. The ridge 24 in this embodiment coacts with an annular groove 26 on a connector 28 in essentially the same manner as the shoulder 22 coacts with the barb 20. In heat exchanger/oxygenator units, barbed connectors 18 are usually used for the blood or oxygen connectors of the oxygenator sections, while grooved connectors are usually used for the water connections of the heat exchanger sections.

It is understood that the exemplary dust caps for barbed connectors described herein and shown in the drawings represent only presently preferred embodiments of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A dust cap for medical equipment connectors having an outer end and an annular barb, comprising:
   a) an elongated elastically radially deformable hollow substantially cylindrical body having a substantially cylindrical inner surface;
   b) said cylindrical body having a closed end and an open end;
   c) said substantially cylindrical inner surface having a first portion adjacent said closed end of said body adapted to extend from said outer end of said connector to said barb, and a second portion adjacent said open end of said body adapted to extend beyond said barb along said connector;

d) said first portion having a diameter substantially equal to the diameter of said barb, and said second portion having a diameter smaller than the diameter of said barb, the interface between said first and second portions forming a shoulder adapted to lockingly engage said barb.

2. The dust cap of claim 1, in which said body has, adjacent its closed end, a gripping surface including a thickened nub suitable for positive graspings of said dust cap.

\* \* \* \* \*